United States Patent
Kashima et al.

(10) Patent No.: US 8,939,884 B2
(45) Date of Patent: Jan. 27, 2015

(54) SLEEP AID DEVICE AND METHOD, PROGRAM AND RECORDING MEDIUM

(75) Inventors: Koji Kashima, Kanagawa (JP); Yoshihiro Wakita, Tokyo (JP); Takeshi Yamazaki, Kanagawa (JP); Seiji Wada, Kanagawa (JP); Natsuki Kimura, Tokyo (JP)

(73) Assignee: Sony Corporation, Tokyo (JP)

( * ) Notice: Subject to any disclaimer, the term of this patent is extended or adjusted under 35 U.S.C. 154(b) by 76 days.

(21) Appl. No.: 13/556,947

(22) Filed: Jul. 24, 2012

(65) Prior Publication Data

US 2013/0035541 A1 Feb. 7, 2013

(30) Foreign Application Priority Data

Aug. 2, 2011 (JP) ................. 2011-168973

(51) Int. Cl.
| | |
|---|---|
| *A61M 21/00* | (2006.01) |
| *A61M 21/02* | (2006.01) |
| *A61B 5/0476* | (2006.01) |
| *A61B 5/00* | (2006.01) |
| *A47G 9/10* | (2006.01) |
| *A61B 5/0478* | (2006.01) |

(52) U.S. Cl.
CPC ............. *A61M 21/02* (2013.01); *A61B 5/0476* (2013.01); *A61B 5/4812* (2013.01); *A47G 9/1045* (2013.01); *A61M 2021/0022* (2013.01); *A61M 2021/0027* (2013.01); *A61M 2021/0044* (2013.01); *A61M 2021/0083* (2013.01); *A61M 2230/10* (2013.01); *A61B 5/0478* (2013.01)

USPC ................. 600/26; 600/27; 600/28; 128/897; 128/898; 128/899

(58) Field of Classification Search
USPC ......................... 600/26, 27, 28; 128/897–899
See application file for complete search history.

(56) References Cited

U.S. PATENT DOCUMENTS

| | | | |
|---|---|---|---|
| 6,656,137 B1* | 12/2003 | Tyldsley et al. .................. 601/15 |
| 7,689,274 B2 | 3/2010 | Mullen et al. | |
| 2005/0143617 A1* | 6/2005 | Auphan ........................... 600/26 |
| 2005/0190065 A1* | 9/2005 | Ronnholm .................... 340/575 |
| 2009/0143636 A1* | 6/2009 | Mullen et al. ................... 600/26 |
| 2009/0264715 A1* | 10/2009 | Auphan ........................ 600/301 |
| 2012/0238800 A1* | 9/2012 | Naujokat et al. ................ 600/26 |

FOREIGN PATENT DOCUMENTS

| | | |
|---|---|---|
| JP | SHO 63-019588 | 1/1988 |
| JP | HEI 06-027263 | 2/1994 |

\* cited by examiner

*Primary Examiner* — Christine Matthews
*Assistant Examiner* — Sunita Reddy
(74) *Attorney, Agent, or Firm* — K&L Gates LLP

(57) ABSTRACT

Disclosed herein is a sleep aid device including: an electrode arranged on the surface of a pillow in such a manner as to come into contact with the scalp of a user; a brain wave signal acquisition section adapted to acquire a brain wave signal of the user via the electrode; an analysis section adapted to analyze the acquired brain wave signal; and a control section adapted to control the execution of a preset process according to the sleep stage representing the depth of sleep of the user identified by the analysis result.

12 Claims, 6 Drawing Sheets

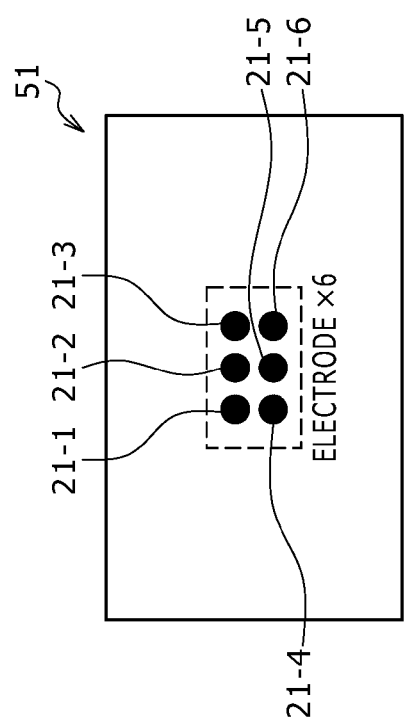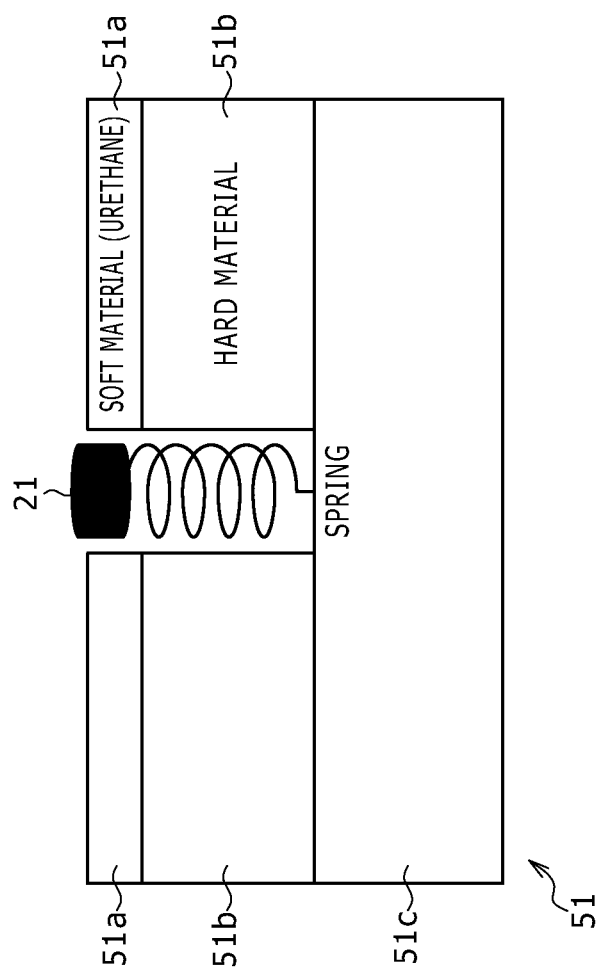

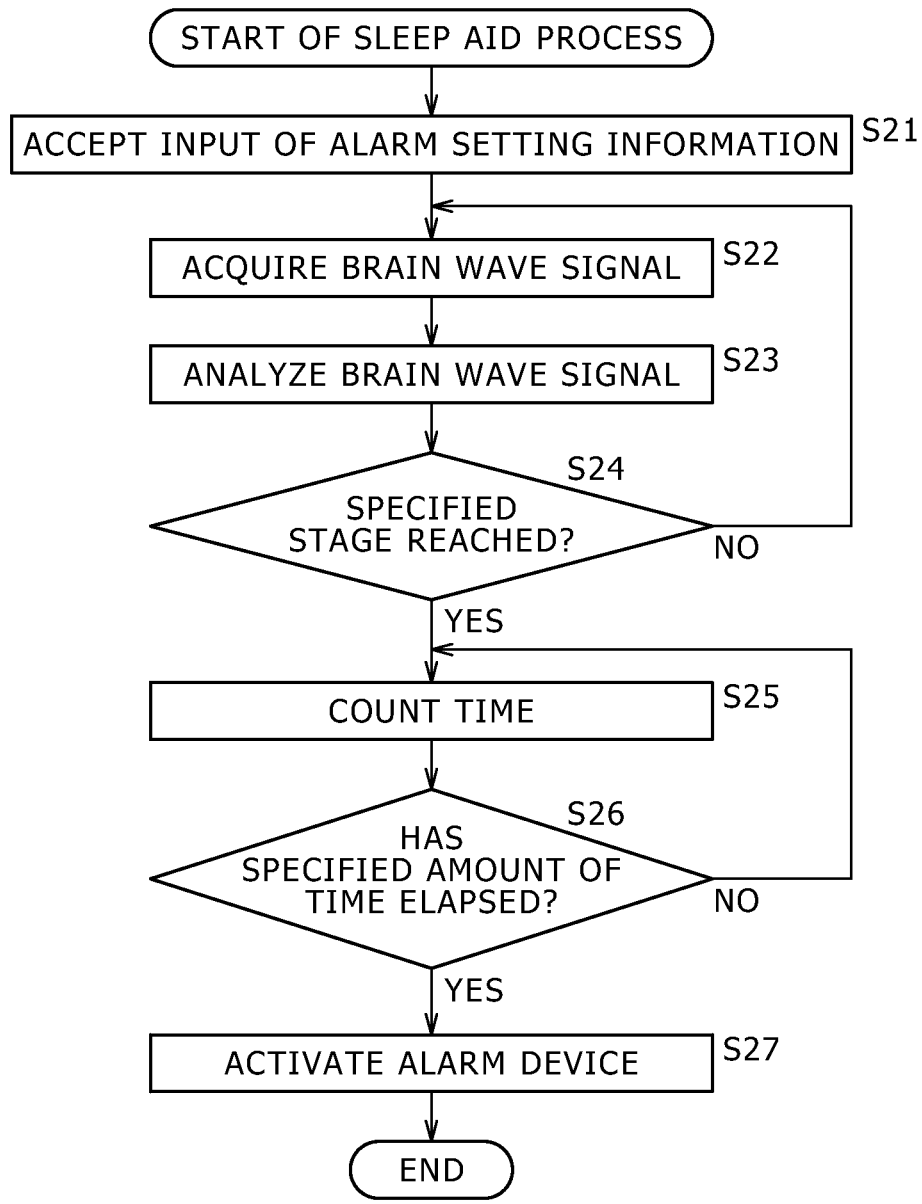

SLEEP AID DEVICE AND METHOD, PROGRAM AND RECORDING MEDIUM

CROSS REFERENCES TO RELATED APPLICATIONS

The present application claims priority to Japanese Priority Patent Application JP 2011-168973 filed in the Japan Patent Office on Aug. 2, 2011, the entire content of which is hereby incorporated by reference.

BACKGROUND

The present application relates to a sleep aid device and method, program and recording medium, and more particularly, to a sleep aid device and method, program and recording medium for having a short sleep efficiently.

Recent years have seen attention focused on the efficacy of a daytime nap. It is said that 15 to 20 minutes of sleep, for example, provides improved efficiency in afternoon work and study.

For example, it is necessary to decide in how many minutes from now to wake up and set an alarm clock before taking a daytime nap at a workplace or school.

Further, a technique has been proposed to significantly reduce discomfort at the time of waking up by detecting a REM sleep condition of a person at sleep and waking up that person in a shallow sleep time zone close to a REM sleep condition before the final get-up time (refer, for example, to Japanese Patent Laid-Open No. 1994-27263).

Still further, the detection of the sleep stage according to the body movement is also conducted (refer, for example, to Japanese Patent Laid-Open No. 1988-19588).

Still further, it has been proposed to receive brain activity data, determine the sleep level from the brain activity data and sound an alarm, for example, if it is determined that the awakening point has been reached when the sleepiness level is sufficiently high (refer, for example, to U.S. Pat. No. 7,689, 274).

SUMMARY

However, how quickly a person falls asleep varies from one person to another and depends on the mind and body condition and surrounding environment. As a result, for example, if a person has difficulty falling asleep, the alarm clock may sound when the person has had only a very short sleep.

The present application is disclosed in light of the foregoing, and it is desirable to allow a person to have a short sleep efficiently irrespective of the time or location.

A mode of the present application is a sleep aid device that includes an electrode, brain wave signal acquisition section, analysis section and control section. The electrode is arranged on the surface of a pillow in such a manner as to come into contact with the scalp of a user. The brain wave signal acquisition section acquires a brain wave signal of the user via the electrode. The analysis section analyzes the acquired brain wave signal. The control section controls the execution of a preset process according to the sleep stage representing the depth of sleep of the user identified by the analysis result.

The control section can start time counting when it is determined that the sleep stage has reached a preset stage and control the generation of stimuli adapted to awaken the user when a preset amount of time elapses.

The control section can control the generation of stimuli adapted to prompt the user to fall asleep if it is determined that the sleep stage has yet to reach a preset stage.

The electrode can be arranged on the surface of a pillow that is configured so that the user sleeps with his or her face buried in the pillow.

The pillow is a body pillow in which the electrode can be arranged where it comes into contact with the forehead of the user.

The pillow can be configured to be used as a back of a chair.

Another mode of the present application is a sleep aid method that includes acquiring, with a brain wave signal acquisition section, a brain wave signal of a user via an electrode arranged on the surface of a pillow in such a manner as to come into contact with the scalp of a user. The sleep aid method further includes analyzing, with an analysis section, the acquired brain wave signal. The sleep aid method still further includes controlling, with a control section, the execution of a predetermined process according to the sleep stage representing the depth of sleep of the user identified by the analysis result.

Still another mode of the present application is a program allowing a computer to serve as a sleep aid device that includes an electrode, brain wave signal acquisition section, analysis section and control section. The electrode is arranged on the surface of a pillow in such a manner as to come into contact with the user's scalp. The brain wave signal acquisition section acquires a brain wave signal of the user via the electrode. The analysis section analyzes the acquired brain wave signal. The control section controls the execution of a predetermined process according to the sleep stage representing the depth of sleep of the user identified by the analysis result.

In one mode of the present application, a brain wave signal of a user is acquired via an electrode arranged on the surface of a pillow in such a manner as to come into contact with the scalp of a user. The acquired brain wave signal is analyzed, and the execution of a preset process is controlled according to the sleep stage representing the depth of sleep of the user identified by the analysis result.

The present application allows a person to have a short sleep efficiently irrespective of the time or location.

Additional features and advantages are described herein, and will be apparent from the following detailed description and the figures.

BRIEF DESCRIPTION OF THE FIGURES

FIGS. 4A and 4B are diagrams describing how the electrode shown in FIG. 2 is mounted to the pillow;

FIG. 5 is a flowchart describing an example of a sleep aid process;

DETAILED DESCRIPTION

A description will be given below of the preferred embodiment of the application disclosed in the present specification with reference to the accompanying drawings.

Figure 1:
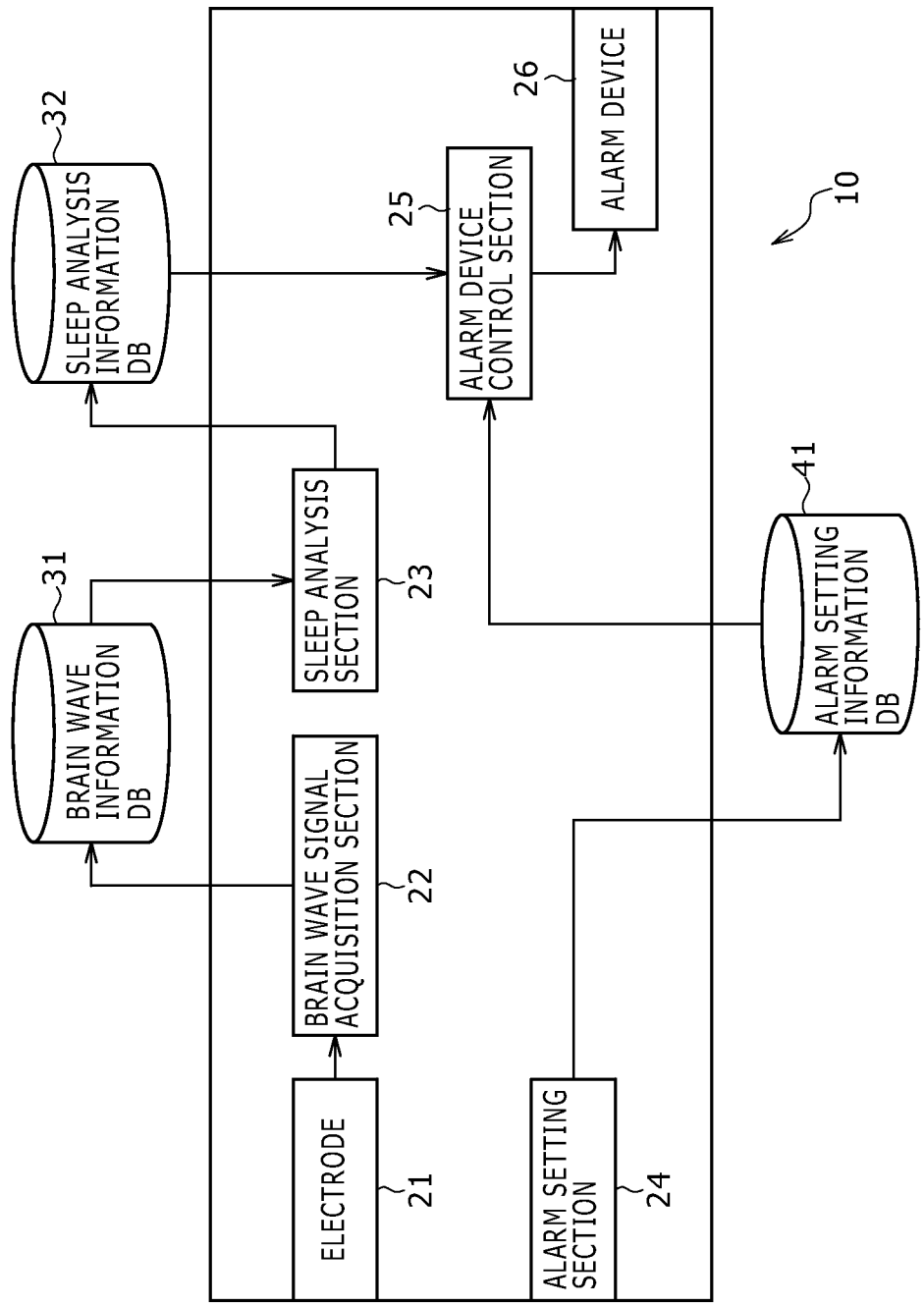
FIG. 1 is a block diagram illustrating a configuration example of a sleep aid device according to an embodiment of the present application.

FIG. 1 is a block diagram illustrating a configuration example of a sleep aid device according to an embodiment of the present application. A sleep aid device 10 determines the sleep stage of a user by measuring his or her brain wave signal and awakens the user, for example, by sounding an alarm when a predetermined amount of time elapses after the user falls asleep. The sleep aid device 10 is mounted, for example, inside the pillow.

As illustrated in FIG. 1, the sleep aid device 10 includes an electrode 21, brain wave signal acquisition section 22, sleep analysis section 23, alarm setting section 24, alarm device control section 25 and alarm device 26. Further, a brain wave information database 31, sleep analysis information database 32 and alarm setting information database 41 are provided. The brain wave information database 31 accumulates brain wave information. The sleep analysis information database 32 accumulates sleep analysis information. The alarm setting information database 41 accumulates alarm setting information. It should be noted that the same databases 31, 32 and 41 may be provided in an external storage device.

The electrode 21 is provided in such a manner as to come into contact with a predetermined position of the user's head (e.g., forehead) and connected to the brain wave signal acquisition section 22.

A so-called dry sensor electrode should preferably be used as the electrode 21 of the sleep aid device 10.

When a brain wave is measured, it is common to use a conductive adhesive gel to attach the electrode to the scalp. However, when a conductive adhesive gel is used, a long preparation time is necessary including that for attaching the electrode. Moreover, a conductive adhesive gel makes a subject annoyed or uncomfortable because of its viscosity. A dry sensor electrode is designed to measure a brain wave signal without using any conductive gel.

Further, in order to acquire a brain wave signal with high accuracy, it is necessary to press the electrode 21 onto the forehead or other part of the user's body. Therefore, the electrode 21 is provided, for example, in such a manner as to reduce the discomfort of the user. It should be noted that an example of how the electrode 21 is to be mounted will be described later.

The brain wave signal acquisition section 22 acquires, for example, a signal obtained based on the change in potential of the electrode 21 as a brain wave signal of the user. The same section 22 generates brain wave information, for example, by sampling the acquired brain wave signal at predetermined intervals, thus recording the generated brain wave information to the brain wave information database 31.

The sleep analysis section 23 reproduces the brain wave signal of the user by reading brain wave information accumulated in the brain wave information database 31. At the same time, the same section 23 filters the brain wave signal as necessary, thus removing noise from the brain wave signal. The sleep analysis section 23 determines the sleep stage of the user, for example, by detecting alpha and delta waves in the brain wave signal of the user.

Human sleep has cycles, and these cycles are classified into several stages. For example, human sleep is divided into a total of five stages, namely, one stage of REM sleep and four stages of non-REM sleep. In each of these stages, the bodily functions undergo a slight change. That is, it is possible to identify the depth of human sleep by detecting the above sleep stages.

The sleep analysis section 23 determines the sleep stage of the user by detecting feature quantities of the brain wave signal necessary to identify each stage. Intensities of the above-mentioned alpha and delta waves contained in the brain wave signal and distinctive waveform are, for example, used as feature quantities adapted to identify each stage.

The sleep analysis section 23 generates, for example, information correlated with the time of transition of the sleep stage for each user as an analysis result. Then, the generated information is recorded to the sleep analysis information database 32 as sleep analysis information.

The alarm setting section 24 accepts, for example, a setting in relation to the time at which the user is to be awakened. For example, information such as "10 minutes after the user's sleep reaches stage 2" is set as a time for awakening the user. This information is used as alarm setting information. Alarm setting information accepted by the alarm setting section 24 is recorded to the alarm setting information database 41.

The alarm device control section 25 controls the alarm device 26 based on the sleep analysis information accumulated in the sleep analysis information database 32 and alarm setting information accumulated in the alarm setting information database 41.

The alarm device 26 includes, for example, a speaker adapted to produce an alarm sound, lamp adapted to shine light and motor adapted to produce vibrations, thus applying stimuli adapted to awaken the user at sleep.

The alarm device control section 25 operates, for example, in the following manner based on alarm setting information. For example, the same section 25 identifies the time at which the user's sleep reached stage 2 based on the sleep analysis information and activates the alarm device 26 in 10 minutes after that time. As a result, the user will be awakened in 10 minutes after his or her sleep reaches stage 2.

Sleeping deep (e.g., stage 3 or 4) at daytime is likely to cause inconveniences such as making sleeping at night difficult and feeling spaced-out. In contrast, having a proper depth of sleep (e.g., stage 1 or 2) at daytime for a short period of time is said to be highly effective for recovery from fatigue, providing improved efficiency at work or study after being awakened.

The present application awakens the user by identifying the sleep stage based on the user's brain waves, thus allowing the user to sleep in such a manner as to achieve improved efficiency at work or study after being awakened.

It should be noted that if the user's sleep has yet to reach, for example, stage 1 or 2 as a result of analysis by the sleep analysis section 23, the alarm device control section 25 may control the alarm device 26 in such a manner as to aid the user to fall asleep. For example, the alarm device 26 may produce a soothing environmental sound from a speaker or release a highly relaxing scent.

Alternatively, the alarm device 26 may be controlled to ensure that the user does not sleep deep. For example, if the user's sleep has reached, for example, stage 3 as a result of analysis by the sleep analysis section 23, stimuli such as gentle vibrations may be applied to the user to an extent of not waking him or her up so as to bring the user into shallower sleep (e.g., stage 1 or 2).

Figure 2:
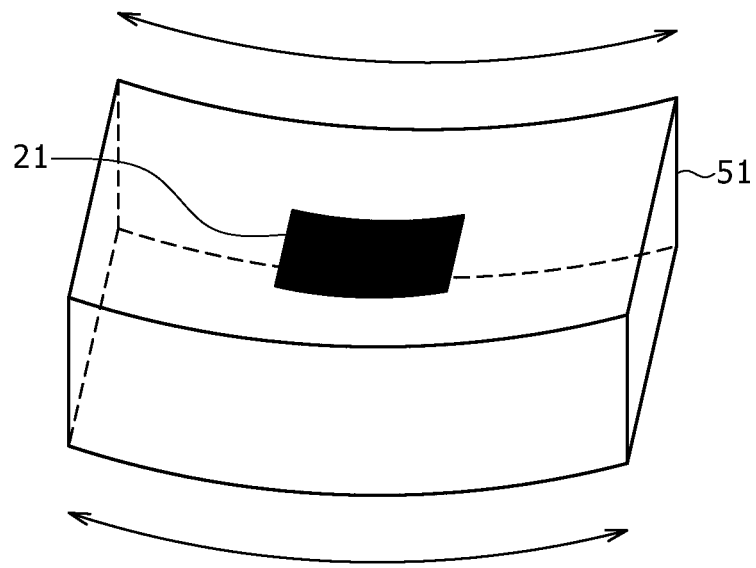
FIG. 2 is a diagram illustrating an example of appearance of a pillow to which the sleep aid device is mounted.

FIG. 2 is a diagram illustrating an example of appearance of a pillow to which the sleep aid device 10 is mounted. A pillow 51 shown in FIG. 2 is configured so that the user sleeps in such a manner as to bury his or her face in the pillow 51 with the forehead resting on the top side of the pillow. Further, the bottom side of the pillow 51 shown in FIG. 2 is configured to be brought into contact, for example, with a desk.

Figure 3:
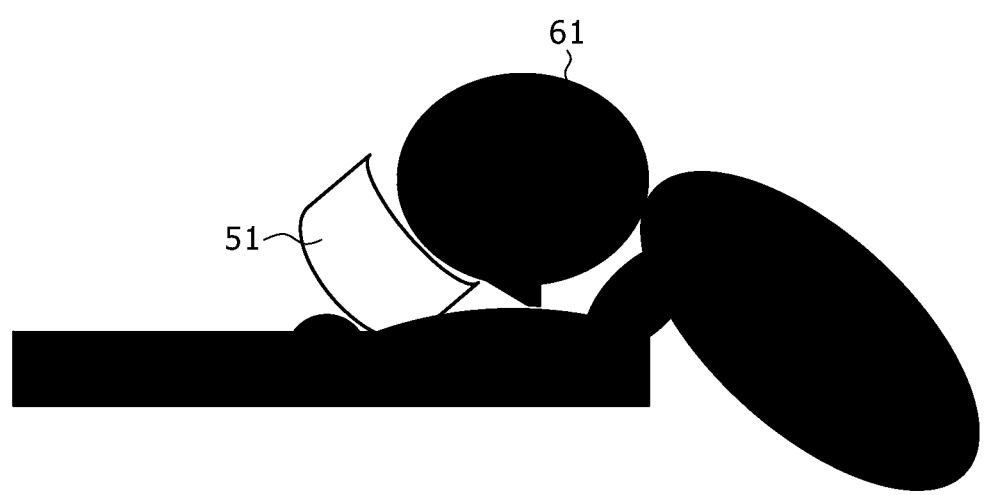
FIG. 3 is a diagram describing an example of using the pillow shown in FIG. 2.

The pillow 51 has its center more or less depressed with the top and bottom sides shown in FIG. 2 curved. Further, the bottom side of the pillow 51 is curved in another direction as shown in FIG. 3 which will be described later. Still further, a cushion is provided, for example, in such a manner as to cover the top side of the pillow 51 shown in FIG. 2 so that the electrode 21 is externally exposed near the center of the pillow 51.

The pillow 51 is configured to be arranged, for example, on a desk so that the user places his or her head 61 on the pillow 51 in such a manner as to bury the face in the pillow 51. The pillow 51 is suitable for taking a short nap, for example, in the middle of work or study.

The bottom side of the pillow 51 is curved as described above so that the user can readily find a body position that makes it easy for him or her to sleep. Further, the head 61 of the user gently sways with the pillow 51 during sleep, thus providing comfortable sleep.

FIGS. 4A and 4B are diagrams describing how the electrode 21 shown in FIG. 2 is actually mounted to the pillow 51. FIG. 4A is a side view of the pillow 51, and FIG. 4B is a top view thereof. It should be noted that the sides of the pillow 51 that are curved in reality are drawn as being straight for reasons of convenience.

As shown in FIG. 4A, the pillow 51 includes a front layer 51a, intermediate layer 51b and bottom layer 51c. The front layer 51a is made of a soft material (e.g., urethane) that serves as a cushion. The intermediate layer 51b is made of a material harder than the front layer 51a.

The electrode 21 is arranged at a slightly higher position than the surface of the front layer 51a in FIG. 4A, with a spring 52 provided under the electrode 21. When the user brings his or her forehead into contact with the electrode 21, the electrode 21 sinks downward. This ensures that the electrode 21 is pressed onto the forehead or other part of the body of the user, thus reducing the discomfort of the user.

Alternatively, there may be the plurality of electrodes 21 mounted to the pillow 51 as illustrated in FIG. 4B rather than the single electrode 21. In the example shown in FIG. 4B, the pillow 51 has six electrodes (21-1 to 21-6). Each of the electrodes 21-1 to 21-6 is mounted as described above with reference to FIG. 4A.

It should be noted that the above examples described with reference to FIGS. 2 to 4 are merely examples of the pillow 51 and electrode 21. Therefore, a pillow and electrode configured in a different manner may be used.

In order to acquire a brain wave signal with high accuracy, it is necessary to maintain the electrode 21 stably in contact with a given position of the user's scalp. For example, it is common to use, for example, a headset so as to maintain the electrode 21 stably in contact with a given position of the user's scalp. However, it is uncomfortable to take a nap wearing a headset. Further, it is troublesome to put on a headset before taking a nap.

When the user takes a nap in a position as shown in FIG. 3, the user's forehead is pressed against the electrode 21, thus allowing the electrode 21 to be maintained stably in contact with a given position of the user's scalp. Therefore, it is possible to acquire the user's brain wave signal during a nap with high accuracy.

That is, the embodiment of the present application allows acquisition of a brain wave of the user at sleep by means of an electrode arranged where his or her head is to be placed. The time at which to awaken the user is determined based on the acquired brain wave signal. This makes it possible to have a short sleep efficiently without any particular preparation and irrespective of the time or location.

FIG. 5 is a flowchart describing an example of a sleep aid process performed by the sleep aid device 10 shown in FIG. 1. This process is performed, for example, if the user takes a short nap using the pillow 51 shown in FIG. 2. It should be noted that we assume here that the sleep aid device 10 is mounted inside the pillow 51 shown in FIG. 2.

In step S21, the alarm setting section 24 accepts input of alarm setting information. At this time, information such as "10 minutes after the user's sleep reaches stage 2" is input. Input alarm setting information is recorded to the alarm setting information database 41.

In step S22, the brain wave signal acquisition section 22 acquires, for example, a signal obtained based on the potential change of the electrode 21 as a brain wave signal of the user. The brain wave signal acquisition section 22 generates brain wave signal, for example, by sampling the acquired brain wave signal at predetermined intervals, thus recording the generated brain wave information to the brain wave information database 31.

In step S23, the sleep analysis section 23 analyzes the brain wave signal acquired in step S22. At this time, the same section 23 reproduces the brain wave signal of the user by reading brain wave information accumulated in the brain wave information database 31. At the same time, the sleep analysis section 23 filters the brain wave signal as necessary, thus removing noise from the brain wave signal. The same section 23 determines the sleep stage of the user, for example, by detecting alpha and delta waves in the brain wave signal of the user.

Next, the sleep analysis section 23 generates, for example, information correlated with the time of transition of the sleep stage for each user as an analysis result. Then, the generated information is recorded to the sleep analysis information database 32 as sleep analysis information.

In step S24, the alarm device control section 25 determines whether the user's sleep has reached the stage specified by the alarm setting information. At this time, for example, the same section 25 identifies, based on the alarm setting information, that the stage specified by the user is stage 2. The alarm device control section 25 determines based on the sleep analysis information whether the user's sleep has reached stage 2.

In step S25, the alarm device control section 25 counts the time.

In step S26, the alarm device control section 25 determines whether the amount of time specified by the alarm setting information has elapsed.

If it is determined in step S26 that the specified amount of time has yet to elapse, the process returns to step S22.

When it is determined in step S26 that the specified amount of time has elapsed, the process proceeds to step S27.

In step S27, the alarm device control section 25 activates the alarm device 26. This, for example, produces an alarm sound, thus awakening the user.

The sleep aid process is performed as described above.

Figure 6:
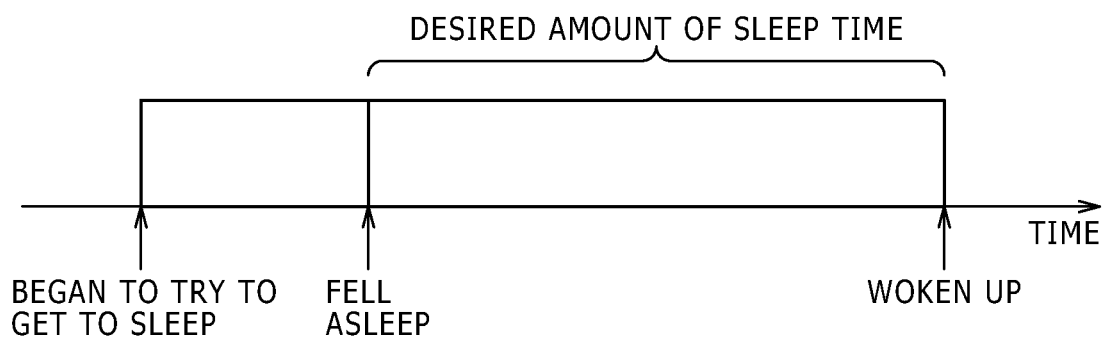
FIG. 6 is a diagram describing how to take a nap when the present application is used.

Thus, the embodiment of the present application determines the sleep stage and awakens the user in a predetermined amount of time. This allows the user to take a nap in a more comfortable manner than doing so by setting an alarm to go off at a specific time. For example, it becomes possible to "wake up" the user in a predetermined amount of time from when the user "fell asleep," and not from when the user "began to try to get to sleep" as illustrated in FIG. 6. This allows the user to "sleep for a desired amount of time" in a reliable manner.

Further, for example, it is possible to produce a soothing environmental sound from a speaker or release a highly relaxing scent to match the detected sleep stage. As described above, the embodiment of the present application provides an efficient way to have a short sleep irrespective of the time or location.

It should be noted that a case was described in the example described above with reference to FIG. 3 in which the sleep aid device 10 is incorporated in the pillow 51 which is configured to be arranged, for example, on a desk so that the user takes a nap with his or her face buried in the pillow 51. However, the sleep aid device 10 may be incorporated in a pillow in other shape. For example, the same device 10 may be incorporated in a body pillow.

Figure 7:
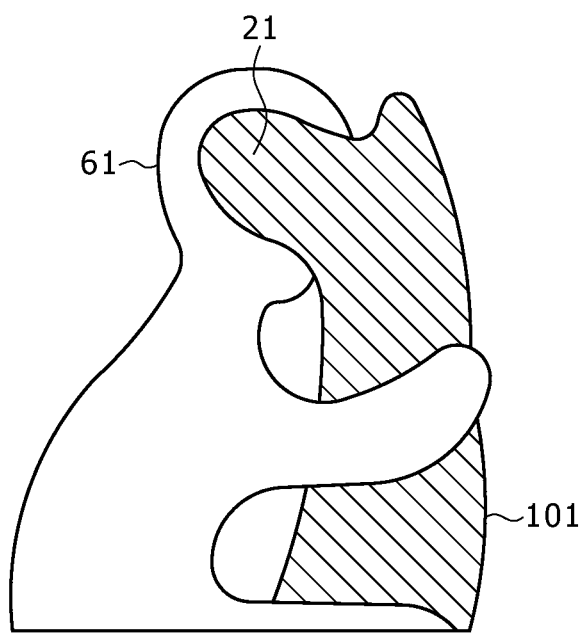
FIG. 7 is a diagram describing another example of a pillow to which the sleep aid device shown in FIG. 1 is mounted.

FIG. 7 is a diagram describing an example in which the sleep aid device 10 according to the present application is incorporated in a body pillow 101. The body pillow 101 shown in FIG. 7 is configured so that the user takes a nap with the pillow held in his or her arms. Further, the pillow 101 has the electrode 21 arranged in the area against which the user presses the forehead of his or her head 61.

This maintains the electrode 21 stably in contact with a given position of the user's scalp, thus making it possible to acquire a brain wave signal of the user taking a nap.

Alternatively, for example, the pillow 101 may be configured to be used as a back of a chair. We assume, for example, an office chair with a high back. We also assume that the back is configured to be used as the pillow 101. When the user takes a nap, he or she sits on the chair in such a manner as to hug the back and bring his or her head 61 into contact with the top side of the body pillow 101.

As described above, the body pillow 101 may be configured to be used as a back of a chair. This also maintains the electrode 21 stably in contact with a given position of the user's scalp, thus making it possible to acquire a brain wave signal of the user taking a nap.

It should be noted that the above series of processes may be performed by hardware or software. If the series of processes are performed by software, the program making up the software is installed from a network or a program recording medium to a computer incorporated in dedicated hardware or a general-purpose personal computer 700 as shown in FIG. 8 capable of performing various functions when installed with various programs.

Figure 8:
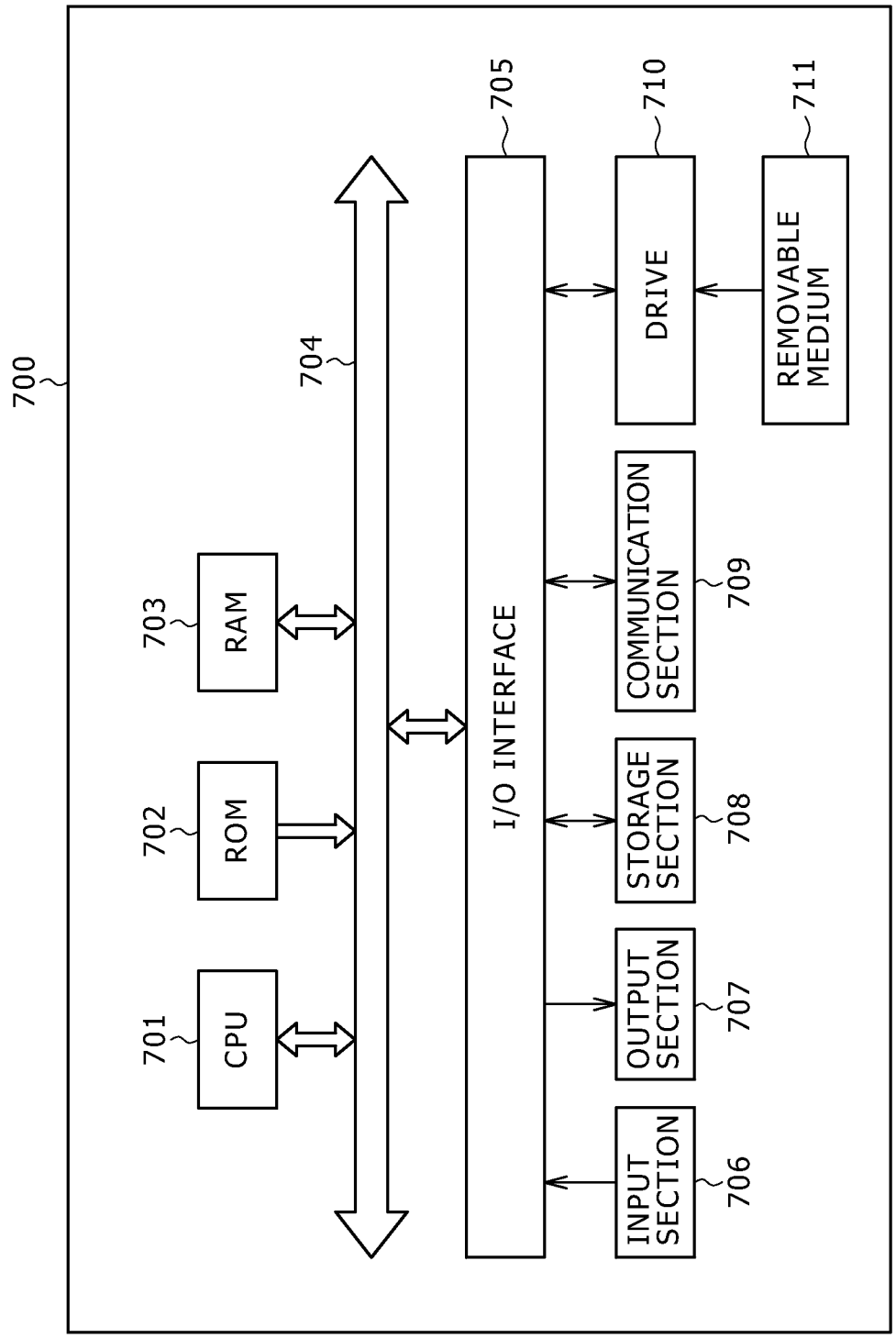
FIG. 8 is a block diagram illustrating a configuration example of a personal computer.

In FIG. 8, a CPU (Central Processing Unit) 701 performs various processes according to the program stored in a ROM (Read Only Memory) 702 or that loaded from a storage section 708 into a RAM (Random Access Memory) 703. The RAM 703 also stores, as appropriate, data necessary for the CPU 701 to perform various processes.

The CPU (Central Processing Unit) 701, ROM (Read Only Memory) 702 and RAM (Random Access Memory) 703 are connected to each other via a bus 704. An I/O interface 705 is also connected to the bus 704.

An input section 706, output section 707, the storage section 708 and a communication section 709 are connected to the I/O interface 705. The input section 706 includes, for example, a keyboard and mouse. The output section 707 includes, for example, a display and speaker. The display includes, for example, an LCD (Liquid Crystal Display). The storage section 708 includes, for example, a hard disk. The communication section 709 includes, for example, a modem and network interface card such as LAN card. The same section 709 handles communication via networks including the Internet.

A drive 710 is also connected, as necessary, to the I/O interface 705. A removable medium 711 such as magnetic disk, optical disk, magneto-optical disk, or semiconductor memory is inserted, as appropriate, into the drive 710. The computer program read from the removable medium 711 is installed, as necessary, to the storage section 708.

If the above series of processes are performed by software, the program making up the software is installed from a network such as the Internet or a recording medium such as the removable medium 711.

It should be noted that this recording medium includes those made up of the removable medium 711 that are distributed separately from the personal computer 700 to deliver the program to the user such as a magnetic disk (including floppy disk (registered trademark)), optical disk (including CD-ROM (Compact Disk-Read Only Memory) and DVD (Digital Versatile Disk)), magneto-optical disk (MD (Mini Disk) (registered trademark)) and a semiconductor memory. This recording medium also includes those that are delivered to the user preinstalled in the personal computer 700 such as the ROM 702 storing the program and the hard disk contained in the storage section 708.

It should be noted that the above series of processes described in the present specification include not only those performed chronologically according to the described sequence but also those that are not necessarily performed chronologically but in parallel or individually.

On the other hand, the embodiments of the present application are not limited to that described above but may be modified in various ways without departing from the scope of the present application.

It should be noted that the present application may have the following configurations.

(1) A sleep aid device including:

an electrode arranged on the surface of a pillow in such a manner as to come into contact with the scalp of a user;

a brain wave signal acquisition section adapted to acquire a brain wave signal of the user via the electrode;

an analysis section adapted to analyze the acquired brain wave signal; and a control section adapted to control the execution of a preset process according to the sleep stage representing the depth of sleep of the user identified by the analysis result.

(2) The sleep aid device of feature 1, in which the control section starts time counting when it is determined that the sleep stage has reached a preset stage, and in which the control section controls the generation of stimuli to awaken the user when a preset amount of time elapses.

(3) The sleep aid device of feature 1 or 2, in which the control section controls the generation of stimuli adapted to prompt the user to fall asleep if it is determined that the sleep stage has yet to reach a preset stage.

(4) The sleep aid device of any one of features 1 to 3, in which the electrode is arranged on the surface of the pillow that is configured so that the user sleeps with his or her face buried in the pillow.

(5) The sleep aid device of any one of features 1 to 4, in which the pillow is a body pillow in which the electrode is arranged where it comes into contact with the forehead of the user.

(6) The sleep aid device of any one of features 1 to 5, in which the pillow is configured to be used as a back of a chair.

(7) A sleep aid method including:

acquiring, with a brain wave signal acquisition section, a brain wave signal of a user via an electrode arranged on the surface of a pillow in such a manner as to come into contact with the scalp of a user;

analyzing, with an analysis section, the acquired brain wave signal; and controlling, with a control section, the execution of a predetermined process according to the sleep stage representing the depth of sleep of the user identified by the analysis result.

(8) A program allowing a computer to serve as a sleep aid device, the sleep aid device including:

an electrode arranged on the surface of a pillow in such a manner as to come into contact with the scalp of a user;

a brain wave signal acquisition section adapted to acquire a brain wave signal of the user via the electrode;

an analysis section adapted to analyze the acquired brain wave signal; and a control section adapted to control the execution of a preset process according to the sleep stage representing the depth of sleep of the user identified by the analysis result.

(9) A recording medium on which the program of feature 8 is recorded.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A sleep aid device comprising:
a pillow comprising:
   an electrode on a surface of the pillow; and
   a spring;
   wherein the spring is in contact with the electrode and the spring is configured to move the electrode up and down within the pillow; and
   wherein the electrode is configured to come into contact with a scalp of a user;
a brain wave signal acquisition section adapted to acquire a brain wave signal of the user via the electrode;
an analysis section adapted to analyze the acquired brain wave signal; and
a control section adapted to control an execution of a preset process according to a sleep stage representing a depth of sleep of the user identified by the analyzed acquired brain wave signal.

2. The sleep aid device of claim 1, wherein
the control section starts time counting when it is determined that the sleep stage has reached a preset stage, and
the control section controls a generation of stimuli to awaken the user when a preset amount of time elapses.

3. The sleep aid device of claim 1, wherein
the control section controls a generation of stimuli adapted to prompt the user to fall asleep if it is determined that the sleep stage has yet to reach a preset stage.

4. The sleep aid device of claim 1, wherein
the electrode on the surface of the pillow is configured for the user to sleep with his or her face buried in the pillow.

5. The sleep aid device of claim 1, wherein
the pillow is a body pillow and the electrode within the body pillow is configured to come into contact with a forehead of the user.

6. The sleep aid device of claim 1, wherein
the pillow is configured to be used as a back of a chair.

7. The sleep aid device of claim 1 further comprising:
a brain wave information database configured to accumulate brain wave information.

8. The sleep aid device of claim 1 further comprising:
a sleep analysis information database configured to accumulate sleep analysis information.

9. The sleep aid device of claim 1 further comprising:
an alarm setting information database configured to accumulate alarm setting information.

10. The sleep aid device of claim 1, wherein the analysis section determines the sleep stage of the user by detecting feature quantities of the acquired brain wave signal.

11. The sleep aid device of claim 10, wherein the feature quantities can include intensities of alpha and delta waves contained in the acquired brain wave signal or distinctive waveform contained in the acquired brain wave signal.

12. A non-transitory computer recording medium on which a program allowing a computer to serve as a sleep aid device is recorded, the program comprising the steps of:
acquiring, with a brain wave signal acquisition section, a brain wave signal of a user via an electrode arranged on a surface of a pillow;
wherein the electrode is configured to move up and down within the pillow by movement of a spring, wherein the spring is in contact with the electrode, and wherein the electrode is configured to come into contact with a scalp of a user;
analyzing, with an analysis section, the acquired brain wave signal; and
controlling, with a control section, an execution of a preset process according to a sleep stage representing a depth of sleep of the user identified by the analyzed acquired brain wave signal.

* * * * *